(12) United States Patent
Randolph

(10) Patent No.: US 7,091,152 B2
(45) Date of Patent: Aug. 15, 2006

(54) CATALYST COMPOSITION COMPRISING A HETEROPOLY ACID, ZINC, AND A SUPPORT COMPONENT AND PROCESSES THEREFOR AND THEREWITH

(75) Inventor: Bruce B. Randolph, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 410 days.

(21) Appl. No.: 10/350,716

(22) Filed: Jan. 24, 2003

(65) Prior Publication Data

US 2004/0147795 A1    Jul. 29, 2004

(51) Int. Cl.
*B01J 27/14* (2006.01)
*B01J 27/16* (2006.01)
*B01J 27/18* (2006.01)

(52) U.S. Cl. ............... 502/208; 502/210; 502/211; 502/253; 502/200; 502/150

(58) Field of Classification Search ............. 502/208, 502/210, 211, 253
See application file for complete search history.

(56) References Cited

U.S. PATENT DOCUMENTS

| | | | |
|---|---|---|---|
| 3,622,644 A | 11/1971 | Kubicek et al. | |
| 3,691,095 A | 9/1972 | Kroll et al. | |
| 3,954,668 A | 5/1976 | Yoo et al. | |
| 5,300,703 A | 4/1994 | Knifton | |
| 5,324,881 A | 6/1994 | Kresge et al. | |
| 5,336,827 A | 8/1994 | Ohno et al. | |
| 5,475,178 A | 12/1995 | Del Rossi et al. | |
| 5,659,096 A | 8/1997 | Randolph et al. | |
| 5,744,678 A | 4/1998 | Aida et al. | |
| 6,025,295 A * | 2/2000 | Tanielyan et al. | 502/154 |
| 6,596,896 B1 * | 7/2003 | Yoshisato et al. | 558/274 |
| 6,610,195 B1 * | 8/2003 | Masloboishchikova et al. | 208/137 |

* cited by examiner

*Primary Examiner*—Elizabeth D. Wood
(74) *Attorney, Agent, or Firm*—Jeffrey R. Anderson

(57) ABSTRACT

A process of contacting at least one isoparaffin and at least one $C_5$ olefin in the presence of a catalyst composition under conversion conditions to provide for converting the at least one isoparaffin and the at least one $C_5$ olefin is provided. The catalyst composition contains a heteropoly acid, zinc, and a support component.

31 Claims, 6 Drawing Sheets

US 7,091,152 B2

CATALYST COMPOSITION COMPRISING A HETEROPOLY ACID, ZINC, AND A SUPPORT COMPONENT AND PROCESSES THEREFOR AND THEREWITH

BACKGROUND OF THE INVENTION

The present invention relates to a process of contacting an isoparaffin and a $C_5$ olefin in the presence of a catalyst composition.

Numerous catalysts have been disclosed in the prior art as suitable for contacting isoparaffins and olefins containing from about 4 to about 7 carbon atoms per molecule to provide for various converting of such hydrocarbons, particularly to form hydrocarbon products having from about 6 to about 9 carbon atoms per molecule. Hydrocarbons having from about 6 to about 9 carbon atoms have various significant uses, such as increasing the octane of gasoline, improving the distillation index of gasoline, and to provide various oligomeric products that are valuable in either the petrochemical field, the fuel industry, or combinations thereof. However, there is a significant and continuing need to provide catalyst compositions that are useful in increasing the number of hydrocarbons having from about 6 to about 9 carbon atoms per molecule produced from the contacting of isoparaffins and olefins having from about 4 to about 7 carbon atoms per molecule.

Numerous catalysts and processes have also been disclosed in the prior art for isomerizing olefins, such as 1-pentene to 2-pentene. The isomer products can be utilized as additional feed stocks for alkylation units, various chemical processes, and the like. However, there is a significant and continuing need to provide catalyst compositions that are effective in providing for an increase in the yield of isomer products produced from isomerizing olefins.

It is also known in the art that a catalyst composition containing platinum can be utilized for various hydrocarbon reactions and conversions, such as isomerizing, oligomerizing, disproportionating, cleaving, and the like and combinations thereof. However, there is a significant expense associated with the use of platinum on such catalysts. Thus, catalyst compositions that do not utilize platinum, but which can provide for hydrocarbon production and regenerability similar to platinum-containing catalyst compositions would be of significant contribution to the art and the economy.

It is also known in the art that the use of supported platinum catalyst compositions (such as platinum on alumina) for various hydrocarbon conversion reactions, such as isomerizing hydrocarbons, encounter significant problems with the rapid deactivation of such catalyst compositions. There are believed to be a number of causes of such catalyst deactivation. One such cause of catalyst deactivation is the formation and accumulation of high molecular weight hydrocarbons, such as $C_5$ to $C_{16}$ hydrocarbons, carbon, and/or coke, within the pores of such catalyst compositions, particularly at the reaction sites, also referred to as acid sites, within such catalyst compositions as well as on the surface of such compositions. The formation and accumulation of such high molecular weight hydrocarbons causes a high rate of catalyst deactivation, a short run life of the catalyst, and an unsteady yield of hydrocarbon products. Hydrocarbon conversion reactions and processes that counteract such deactivation would also be of significant contribution to the art and the economy.

SUMMARY OF THE INVENTION

It is an object of the present invention to provide a process for contacting at least one isoparaffin and at least one $C_5$ olefin in the presence of a catalyst composition under conversion conditions to provide for converting the at least one isoparaffin and the at least one $C_5$ olefin. The converting can include, but is not limited to, isomerizing, oligomerizing, disproportionating, cleaving, and the like and combinations thereof The catalyst composition comprises a heteropoly acid, zinc, and a support component.

Another object of the present invention is to provide a process that comprises contacting at least one isoparaffin and at least one $C_5$ olefin in a hydrocarbon-containing fluid in the presence of a catalyst composition under conversion conditions to provide a product comprising a larger amount of hydrocarbons having from about 6 to about 9 carbon atoms per molecule than were present in the hydrocarbon-containing fluid before such contacting.

Another object of the present invention is to provide a process that comprises contacting at least one isoparaffin and at least one $C_5$ olefin in the presence of a catalyst composition, during which such process, deactivation of such catalyst composition occurs, and such process further includes the addition of an organic chloride compound that is useful in countering the deactivation of such catalyst composition.

A further object of the present invention is to provide a method by which the activity or run life of a catalyst composition comprising a heteropoly acid, zinc, and a support component can be enhanced, or essentially prolonged, resulting in a substantially constant conversion of hydrocarbons.

An embodiment of the present invention comprises a process comprising contacting at least one isoparaffin and at least one $C_5$ olefin in the presence of a catalyst composition under conversion conditions to provide for converting the at least one isoparaffin and the at least one $C_5$ olefin, where the converting can include isomerizing, oligomerizing, disproportionating, cleaving and the like and combinations thereof. A catalyst composition of the present invention comprises a heteropoly acid, zinc, and a support component.

Another embodiment of the present invention comprises a catalyst composition comprising a heteropoly acid, zinc, and a support component. Such catalyst composition can be utilized in a variety of conversion processes such as contacting at least one isoparaffin and at least one $C_5$ olefin, where the converting can include isomerizing, oligomerizing, disproportionating, cleaving, and the like and combinations thereof.

A process and catalyst composition of the present invention can offer several benefits, including, but not limited to, (1) the ability to conduct a variety of conversion reactions to provide for hydrocarbons having from about 6 to about 9 carbon atoms per molecule; (2) the ability to obtain conversions and regenerability similar to a platinum-containing catalyst composition; (3) extending the run life of the catalyst, which translates into longer operating runs between catalyst regenerations; and (4) fewer catalyst regeneration cycles, which translates into safer operation, less down time, and greater economic benefit.

Other objects and advantages of the present invention will become apparent from the detailed description and the appended claims.

BRIEF DESCRIPTION OF THE DRAWINGS

In order to assist the understanding of the present invention, reference will now be made to the appended drawings. The drawings are exemplary only and should not be construed as limiting the present invention.

DETAILED DESCRIPTION OF THE INVENTION

Figure 1:
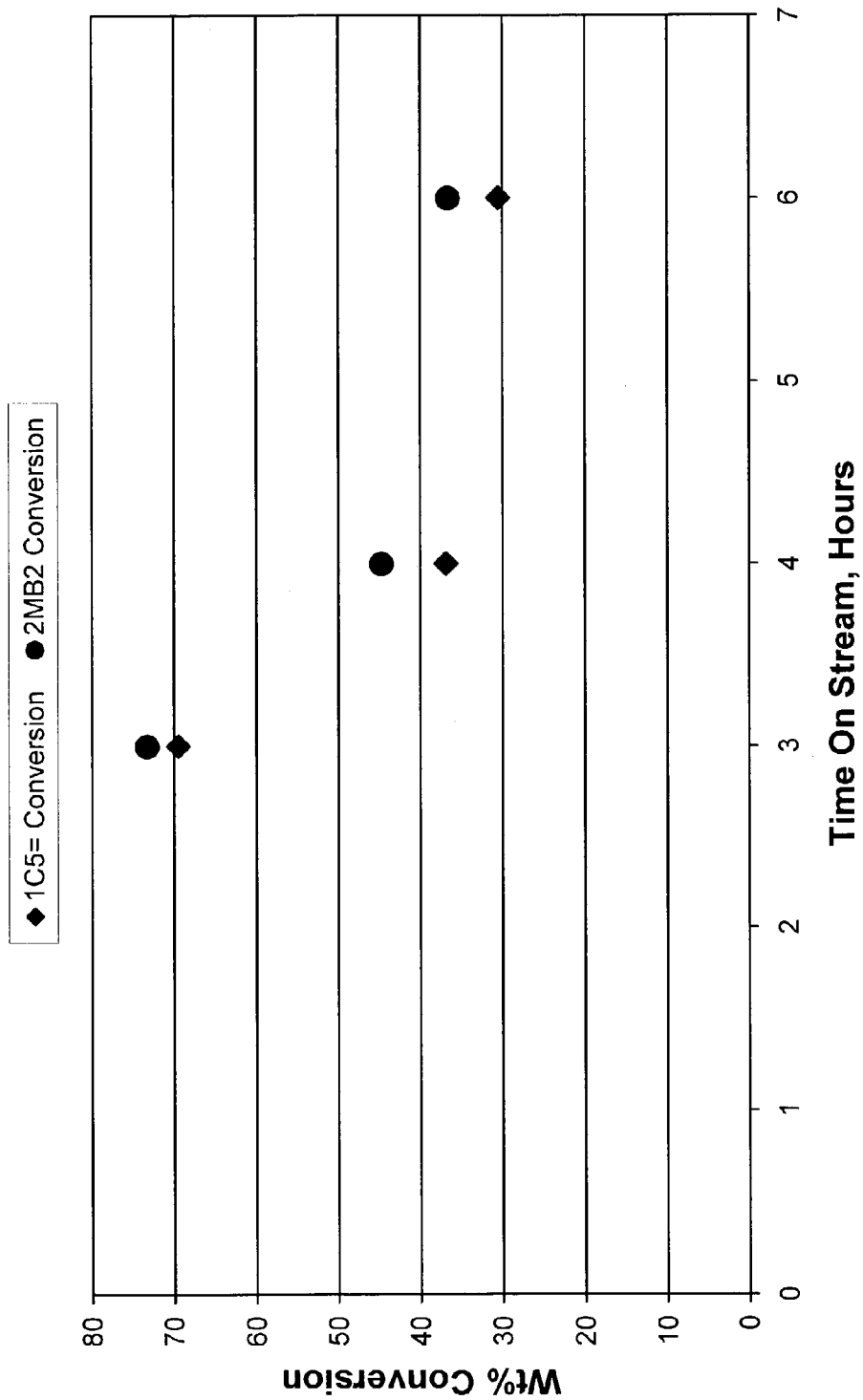
FIG. 1 is a graph of the C5=conversions before the first regeneration of catalyst composition C described herein in Example 1 utilizing the conditions described herein in Example 3 and based on the data disclosed in Table 3.

It has been discovered that a catalyst composition comprising a heteropoly acid, zinc, and a support component can be utilized in a process of the present invention comprising contacting at least one isoparaffin and at least one $C_5$ olefin under conversion conditions to provide for converting the at least one isoparaffin and the at least one $C_5$ olefin. The converting can include, but is not limited to, isomerizing, oligomerizing, disproportionating, cleaving, and the like and combinations thereof.

The term "$C_5$ olefin" as used herein refers to an olefin having 5 carbon atoms per molecule. The $C_5$ olefins that can be utilized in a process of the present invention include any $C_5$ olefins that can be contacted with at least one isoparaffin, according to a process of the present invention. Examples of suitable $C_5$ olefins include, but are not limited to, 1-pentene, 2-methyl-1-butene, 2-methyl-2-butene, and the like and combinations thereof. Preferably, the $C_5$ olefin comprises 1-pentene, 2-methyl-2-butene, and combinations thereof. More preferably, the $C_5$ olefin comprises 1-pentene.

Isoparaffins, also referred to as isoalkanes, that can be utilized in a process of the present invention include any isoparaffin that can be contacted with at least one $C_5$ olefin according to a process of the present invention. Examples of suitable isoparaffins include, but are not limited to, isoparaffins comprising from about 4 to about 7 carbon atoms per molecule. Examples of suitable isoparaffins that can be contacted with at least one $C_5$ olefin utilizing a process of the present invention include, but are not limited to, isobutane, isopentane, 2,2-dimethylbutane, 2,3-dimethylbutane, 2-methylpentane, 3-methylpentane, 2,2-dimethylpentane, 2,4-dimethylpentane, 2,2,3-trimethylbutane, 3,3-dimethylpentane, 2-methylhexane, 2,3-dimethylpentane, 3-methylhexane, 3-ethylpentane, and the like and combinations thereof. Preferably, an isoparaffin contacted with at least one $C_5$ olefin utilizing a process of the present invention comprises isopentane.

Generally, the converting provides for a product comprising hydrocarbons having from about 4 to about 10 carbon atoms per molecule. Preferably, such converting provides for a product comprising hydrocarbons having from about 6 to about 9 carbon atoms per molecule. Also preferred is that the converting provides for a product comprising a larger amount of hydrocarbons having from about 6 to about 9 carbon atoms per molecule than were present before such contacting. A preferred converting comprises isomerizing at least one $C_5$ olefin comprising 1-pentene to provide for an isomer product comprising at least one 2-pentene.

The term "fluid" as used herein refers to gas, liquid, vapor, and combinations thereof.

The term "zinc" as used herein refers to zinc in any form including elemental zinc, a zinc component as described herein, or combinations thereof.

Preferably, contacting at least one isoparaffin and at least one $C_5$ olefin in the presence of a catalyst composition utilizing a process of the present invention provides for a converting of the at least one isoparaffin and the at least one $C_5$ olefin. The term "converting" or "conversion" as used herein refers to any change in a hydrocarbon as described herein as a result of utilizing a process of the present invention. Examples of suitable converting or conversion include, but are not limited to, isomerizing, oligomerizing, disproportionating, cleaving, and the like and combinations thereof. The converting of at least one isoparaffin and at least one $C_5$ olefin according to a process of the present invention can include a variety of conversion reactions that can provide for a variety of hydrocarbon products. It should be understood that the various reactions can be occurring separately, simultaneously, and combinations thereof.

Generally, the reactants comprising at least one isoparaffin and at least one $C_5$ olefin are initially present in a hydrocarbon-containing fluid. However, an additional embodiment of a process of the present invention includes separate feed streams comprising a feed stream comprising at least one isoparaffin, such as a feed stream rich in isoparaffins, and a separate feed stream comprising at least one $C_5$ olefin, that can be fed separately into a reactor and subjected to mixing in the presence of a catalyst composition of the present invention and for converting as described herein. Examples of suitable hydrocarbon-containing fluids include, but are not limited to, fuel gas, gasolines from catalytic oil-cracking (e.g., FCC and hydrocracking) processes, pyrolysis gasolines from thermal hydrocarbon-(e.g., methane, propane, naphtha) cracking processes, naphthas, gas oils, reformates, straight-run gasoline, and the like and combinations thereof.

A heteropoly acid of a catalyst composition of the present invention can be any heteropoly acid that can be utilized to provide a catalyst composition that can be utilized in a process of the present invention. Generally, a heteropoly acid comprises a class of acids formed by the condensation of two or more inorganic oxyacids. For example, phosphate and molybdenum ions, when reacted in an acidic medium, are condensed to form 12-molybdophosphoric acid, a typical heteropoly acid. A wide variety of elements ranging from Group I to Group VIII of the Periodic Table of the Elements can become the central atom of the heteropoly acid anion, also referred to as the heteroatom, (e.g., phosphorus, in the case of 12-molybdophosphoric acid). The nature of the heteroatom is a governing factor that determines both the condensation structure and the physical properties of the heteropoly acid. Atoms coordinated to the heteroatom via oxygens are called polyatoms, also referred to as the coordinating element, (e.g., molybdenum, in the case of 12-molybdophosphoric acid) and in most cases are any of one of such limited species as molybdenum, tungsten, niobium, and vanadium. A particular class of heteropoly acids is the protonated form of heteropolymolybdates. These anions contain from 2 to about 18 hexavalent molybdenum atoms around one or more central atoms. Another class of heteropoly acids, which is analogous to the protonated form of heteropolymolybdates, is the protonated form of heteropolytungstates. In heteropolytungstates, the polyatom or coordinating element is tungsten, instead of molybdenum. Examples of a suitable heteropoly acid include, but are not limited to, 12-molybdophosphoric acid, 12-tungstophosphoric acid, molybdosilicic acid, 12-tungstosilicic acid, and the like and combinations thereof. Preferably, a heteropoly acid is 12-molybdophosphoric acid.

A support component of a catalyst composition of the present invention can be any support component that suitably provides for a catalyst composition of the present invention that can be utilized in a process of the present invention. A support component of a catalyst composition of the present invention can be any inorganic metal oxide that is typically used as a catalytic support material. Examples of a suitable support component include, but are not limited to, alumina, silica, aluminasilicates, activated carbon, zeolites, oxides of the metals of Groups II, III, IV, V, and VI A of the Periodic Table of the Elements, and the like and combinations thereof. The oxides of the metals of Groups II, III B and IV B of the Periodic Table of the Elements are preferred, such as alumina, boria, zinc oxide, magnesia, calcium oxide, strontium oxide, barium oxide, titania, zirconia, vanadia, and the like and combinations thereof. The support component can be synthetically prepared or can be a naturally occurring support material, such as naturally occurring clays, kieselguhr, diatomaceous earth, zeolites, silica, thoria, zirconia, and the like and combinations thereof. Preferably, a support component of a catalyst composition of the present invention comprises alumina.

Alumina suitable for use in a catalyst composition of the present invention can be characterized by having the following characteristics. Generally, the surface area of the alumina is in the range of from about 5 $m^2/g$ (measured by the Brunauer, Emmett, Teller method, i.e., BET method) to about 400 $m^2/g$, preferably in the range of from about 10 $m^2/g$ to about 300 $m^2/g$, and more preferably in the range of from about 50 $m^2/g$ to about 200 $m^2/g$. The pore volume of the alumina is generally in the range of from about 0.05 mL/g to about 2 mL/g, preferably in the range of from about 0.10 mL/g to about 1.5 mL/g, and more preferably in the range of from about 0.20 mL/g to about 1 mL/g. The average pore diameter of the alumina is generally in the range of from about 5 angstroms to about 600 angstroms, preferably in the range of from about 10 angstroms to about 500 angstroms, and more preferably in the range of from about 25 angstroms to about 200 angstroms.

The size and shape of a catalyst composition of the present invention will be based largely on the size and shape of the support component. Preferably, a catalyst composition of the present invention is in the form of tablets, pellets, extrudates, spheres, and the like and combinations thereof. More preferably, the catalyst composition of the present invention is in the form of an extrudate comprising a heteropoly acid, zinc, and a support component, preferably alumina. A catalyst composition of the present invention generally has a particle size in the range of from about 0.1 millimeters (mm) to about 10 mm, preferably in the range of from about 0.5 mm to about 8 mm, and more preferably in the range of from about 1 mm to about 6 mm.

A zinc component of the present invention can be any zinc component that suitably provides for a catalyst composition of the present invention comprising zinc that can be utilized in a process of the present invention. Generally, this will be a reducible zinc salt or zinc oxide. Examples of a suitable zinc component include, but are not limited to, zinc bromide, zinc chloride, zinc iodide, zinc nitrate hydrate, zinc nitrate hexahydrate, zinc nitrate, zinc oxide, zinc perchlorate hexahydrate, zinc sulfate heptahydrate, and the like, and combinations thereof. A preferred zinc component that can be utilized in preparing a catalyst composition of the present invention comprises zinc chloride. It should be understood that the zinc component may be partially or completely converted to elemental zinc during a process of preparing or using a catalyst composition of the present invention.

An amount of zinc component utilized in a process of preparing a catalyst composition of the present invention is such as to provide a concentration of zinc in a catalyst composition of the present invention that can be utilized in contacting at least one isoparaffin and at least one $C_5$ olefin according to a process of the present invention. An amount of zinc component utilized in preparing a catalyst composition of the present invention is such as to provide a concentration of zinc in a catalyst composition of the present invention generally in the range of from about 0.1 weight percent to about 10 percent based on the total weight of the catalyst composition, preferably in the range of from about 0.5 weight percent to about 8 weight percent, and more preferably in the range of from about 1 weight percent to about 6 weight percent.

An amount of support component utilized in a process of preparing a catalyst composition of the present invention can be any amount that suitably provides for a catalyst composition of the present invention that can be utilized in contacting at least one isoparaffin and at least one $C_5$ olefin according to a process of the present invention. An amount of support component, preferably alumina, utilized in preparing a catalyst composition of the present invention is such as to provide a concentration of support component in a catalyst composition of the present invention generally in the range of from about 50 weight percent to about 99.9 weight percent based on the total weight of the catalyst composition, preferably in the range of from about 60 weight percent to about 95 weight percent, and more preferably in the range of from about 70 weight percent to about 90 weight percent.

An amount of heteropoly acid utilized in a process of preparing a catalyst composition of the present invention can be any amount that suitably provides for a catalyst composition of the present invention that can be utilized in contacting at least one isoparaffin and at least one $C_5$ olefin according to the process of the present invention. An amount of heteropoly acid utilized in a process of preparing a catalyst composition of the present invention is such as to provide a concentration of polyatom, preferably molybdenum, in a catalyst composition of the present invention generally in the range of from about 0.1 weight percent to about 10 weight percent based on the total weight of the catalyst composition, preferably in the range of from about 1 weight percent to about 10 weight percent, and more preferably in the range of from about 1 weight percent to about 5 weight percent. It should be understood that during a process of preparing or using a catalyst composition of the present invention, the heteropoly acid may be converted to the individual heteroatom(s) and polyatom(s).

A catalyst composition of the present invention can be prepared by any suitable manner or method(s) that suitably provides for a catalyst composition of the present invention. Generally, a process of preparing a catalyst composition of the present invention comprises contacting a support component as described herein, preferably alumina, with a heteropoly acid and a zinc component as described herein. Examples of suitable contacting include, but are not limited to, impregnation, mixing, and the like in combinations thereof. Generally, contacting a heteropoly acid, a zinc component and a support component according to process of the present invention comprises any impregnation technique known in the art such as incipient wetness impregnation, spray impregnation, and the like and combinations thereof. A preferred impregnation technique is incipient wetness impregnation that includes essentially completely filling the pores of the support component, preferably alumina, with a solution of the heteropoly acid and a solution of the zinc component.

Preferably, the heteropoly acid is an aqueous solution and is preferably soluble in water. The concentration of the heteropoly acid in the solution can range upwardly to the solubility limit of the heteropoly acid in the solvent. Generally, a concentration of the heteropoly acid in the solution can be in the range of from about 1 weight percent to about 99 weight percent, preferably in the range of from about 5 weight percent to about 50 weight percent, and more preferably in the range of from about 5 weight percent to about 25 weight percent. Generally, a weight ratio of support component to heteropoly acid is in the range of from about 0.01:1 to about 20:1, preferably in the range of from about 0.1:1 to about 10:1, and more preferably in the range of from about 0.1:1 to about 5:1.

The solution of the zinc component may be an aqueous solution, an alcohol-containing solution, or a hydrocarbon solution of the zinc component. It is preferred for the zinc component to be soluble in water. The concentration of the zinc component in the solution can range upwardly to the solubility limit of the zinc component in the solvent. Generally, a concentration of the zinc component in the solution can be in the range of from about 1 weight percent to about 99 weight percent, preferably in the range of from about 5 weight percent to about 50 weight percent, and more preferably in the range of from about 5 weight percent to about 25 weight percent. Generally, a weight ratio of support component to zinc component is in the range of from about 0.01:1 to about 20:1, preferably in the range of from about 0.1:1 to about 10:1, and more preferably in the range of from about 0.1:1 to about 5:1.

The heteropoly acid and zinc component as referred to herein can be contacted with a support component of the present invention in any suitable manner so long as a catalyst composition of the present invention can be prepared. Generally, a support component is first impregnated with a zinc component dissolved in an aqueous solution such as deionized water, by incipient wetness impregnation. The support component can also be sprayed with an impregnating solution containing a dissolved zinc component. Generally, the concentration of the zinc component in the impregnating solution is in the range from about 0.1 gm/mL to about 2 gm/mL, preferably in the range of from about 0.2 gm/mL to about 1 gm/mL. The presently preferred zinc component to be used in the impregnating solution is zinc chloride.

Examples of a suitable solvent of the impregnating solution include, but are not limited to, deionized water, an alcohol as described herein, and the like and combinations thereof. The amounts of zinc component utilized are amounts suitable to provide concentrations as described herein of zinc in a catalyst composition of the present invention. Examples of a suitable alcohol include, but are not limited to, methyl alcohol, ethyl alcohol, isopropyl alcohol, and the like and combinations thereof. A preferred impregnating solution of a zinc component comprises zinc chloride dissolved in deionized water.

The support component impregnated with a zinc component can then be impregnated with a heteropoly acid, preferably dissolved in an aqueous solution, such as deionized water, by incipient wetness impregnation. The support component containing a zinc component can also be sprayed with an impregnating solution containing a dissolved heteropoly acid. Generally, the concentration of the heteropoly acid in the impregnating solution is in the range of from about 0.1 gm/mL to about 2 gm/mL, preferably in the range of from about 0.2 gm/mL to about 1 gm/mL. The presently preferred heteropoly acid to be used in the impregnating solution is 12-molybdophosphoric acid. Examples of a suitable solvent of the impregnating solution include, but are not limited to, deionized water and the like and combinations thereof. The amounts of heteropoly acid utilized are amounts suitable to provide concentrations as described herein of a polyatom, preferably molybdenum, in a catalyst composition of the present invention. A preferred impregnating solution of a heteropoly acid comprises a heteropoly acid dissolved in deionized water.

Other examples of a process of preparing a catalyst composition of the present invention include first impregnating a support component with a solution of heteropoly acid as described herein followed by a second impregnation of the support component and heteropoly acid with a zinc component as described herein. Preferably, a support component is simultaneously impregnated with a solution of a zinc component, preferably zinc chloride dissolved in deionized water, and a solution of heteropoly acid, preferably 12-molybdophosphoric acid dissolved in deionized water.

In an example process of preparing a catalyst composition of the present invention, after contacting a support component with a heteropoly acid, preferably a solution of 12-molybdophosphoric acid, and a zinc component, preferably a solution of zinc chloride, the resulting mixture comprising a heteropoly acid, a zinc component, and a support component can then be formed or shaped, preferably extruded or granulated. Any suitable means known to those skilled in the art for forming, preferably extruding, granulating, agglomerating, and the like and combinations thereof, the mixture comprising a heteropoly acid, a zinc component and a support component can be used to achieve the desired formed mixture, preferably extruded mixture (i.e., extrudate), granulated mixture (i.e., granulate), agglomerated mixture (i.e., agglomerate) and the like and combinations thereof. Examples of suitable means for forming include, but are not limited to, means for extruding, means for granulating, means for agglomerating, and the like and combinations thereof. A liquid such as, but not limited to, water, may be used in forming, preferably extruding, granulating, agglomerating, and the like and combinations thereof, the mixture. Suitable means for extruding can include, but are not limited to, such devices as screw extruders (also known as auger extruders or auger-type extruders) and the like.

Suitable means for granulating can include, but are not limited to, wet granulation and dry granulation. Wet granulation comprises mixing dry ingredients such as a heteropoly acid, a zinc component, and a support component with a liquid such as, but not limited to, water. The resulting wet paste is then dried, coarsely ground, and sieved to the desired size using the proper screen size. Dry granulation comprises densifying dry ingredients, such as a heteropoly acid, a zinc component, and a support component, in a heavy-duty tabletinig press to produce granulates which are subsequently crushed to the desired size.

It can be desirable for the formed mixture to be an agglomerate of the mixture of a heteropoly acid, a zinc component and a support component. Any suitable means or methods known by those skilled in the art for forming such an agglomerate, i.e., means for agglomerating, can be used. Examples of suitable means for agglomerating include, but are not limited to, molding, pressing, pelletizing, tumbling, densifying, and the like and combinations thereof. Further discussion of such methods, including extruding means and granulating means, is provided in a section entitled "Size Enlargement" in *Perry's Chemical Engineers' Handbook, Sixth Edition*, published by McGraw-Hill, Inc., copyright 1984, at pages 8–60 through 8–72, which pages are incorporated herein by reference.

For example, the heteropoly acid, zinc component, and support component can be compounded and subsequently shaped (such as by pelletizing, extruding or granulating) into a compounded composition. Generally the particle size of the compounded composition is in the ranges as described herein.

A process of preparing a catalyst composition of the present invention further comprises drying under a drying condition. A "drying condition" as referred to herein includes a temperature generally in the range of from about 20° C. to about 90° C., preferably in the range of from about 20° C. to about 80° C., and more preferably in the range of from about 25° C. to about 70° C. A drying condition further comprises a pressure generally in the range of from about 0 pounds per square inch absolute (psia) to about 200 psia, preferably in the range of from about 1 psia to about 150 psia, and more preferably in the range of from about 2 psia to about 100 psia. A drying condition further comprises a time period generally in the range of from about 0.5 hour to about 40 hours, preferably in the range of from about 0.5 hour to about 30 hours, and more preferably in the range of from about 1 hour to about 20 hours. A drying condition further comprises an atmosphere, suitable for drying as described herein, preferably air.

In a preferred method of preparing a catalyst composition of the present invention, after contacting a heteropoly acid, a zinc component and a support component as described herein, a mixture, preferably a paste, comprising such components is provided and can be subjected to a means for extruding as described herein to provide for a wet extrudate comprising such components that is then subjected to drying under a drying condition as described herein to provide a dried extrudate comprising such components that can then be subjected to a means for granulating as described herein to provide for dried extrudate pellets comprising a heteropoly acid, a zinc component and a support component.

While drying under a drying condition as described herein can provide for a catalyst composition of the present invention, a process of preparing a catalyst composition of the present invention can further comprise calcining under calcining condition. A "calcining condition" as referred to herein includes a temperature generally in the range of from about 100° C. to about 500° C., preferably in the range of from about 150° C. to about 250° C., and more preferably in the range of from about 175° C. to about 225° C. A calcining condition further comprises a pressure generally in the range of from about 0 pounds per square inch absolute (psia) to about 750 psia, preferably in the range of from about 1 psia to about 600 psia, and more preferably in the range of from about 2 psia to about 500 psia. A calcining condition further comprises a time period generally in the range of from about 0.5 hour to about 30 hours, preferably in the range of from about 1 hour to about 20 hours, and more preferably in the range of from about 1 hour to about 10 hours. A calcining condition further comprises an atmosphere selected from the group consisting of an oxygen-containing atmosphere (e.g., air), nitrogen, helium, argon, and the like and combinations thereof. During calcining, substantially all volatile matter (e.g., water and carbonaceous materials) is removed.

It should be understood that the processes of preparing a catalyst composition of the present invention will depend, in part, on the initial form and particle size of the support component. For example, when the support component comprises a powder form such as alumina powder, the resulting mixture after contacting such alumina powder with solutions of heteropoly acid and zinc component, will provide a paste that can be subjected to a means for forming as described herein, such as a means for extruding, to provide for a wet extrudate that can then be subjected to drying under a drying condition as described herein to form a dried extrudate that can then be subjected to another means for forming as described herein, such as a means for granulating, or other methods for changing the size and shape of the dried extrudate into a form and particle size as described herein. Also, for example, when the support component is present in pellets, such as alumina pellets sized from about 1 mm to about 10 mm, once such pellets are contacted with, preferably impregnated with, solutions of a heteropoly acid and a zinc component followed by drying under a drying condition as described herein and, if desired, calcined under a calcining condition as described herein, further shaping and sizing, such as by subjecting to a means for forming as described herein, may not be needed as the resulting catalyst composition will have a size and shape similar to the initial support component before impregnating.

A process of preparing a catalyst composition of the present invention further comprises, after contacting a heteropoly acid, a zinc component, and a support component, according to a process of the present invention, activating under an activating condition that suitably provides for a catalyst composition that can be utilized in a process of the present invention for contacting at least one isoparaffin and at least one $C_5$ olefin. An "activating condition" as referred to herein includes a temperature generally in the range of from about 50° C. to about 500° C., preferably in the range of from about 60° C. to about 400° C., and more preferably in the range of from about 70° C. to about 300° C. An activating condition further comprises a pressure generally in the range of from about 0 pounds per square inch absolute (psia) to about 750 psia, preferably in the range of from about 1 psia to about 500 psia, and more preferably in the range of from about 2 psia to about 400 psia. An activating condition as referred to herein further comprises a time period generally in the range of from about 0.1 hour to about 30 hours, preferably in the range of from about 0.5 hour to about 20 hours, and more preferably in the range of from about 1 hour to about 10 hours. An activating condition further comprises an atmosphere suitable for activating a catalyst composition of the present invention. Examples of a suitable activating atmosphere include, but are not limited to, hydrogen, hydrogen diluted with nitrogen, ammonia, hydrazine, other reducing gases, and the like and combinations thereof. A preferred activating atmosphere is hydrogen. Also, a deactivated catalyst composition as described herein can be reactivated or regenerated by subjecting the deactivated catalyst composition to an activating condition as described herein.

Another example of a suitable activating atmosphere comprises a mixture of hydrogen and an organic chloride compound as described herein. Utilizing a mixture of hydrogen and organic chloride compound can be useful when a conducting a process of the present invention utilizing an organic chloride compound addition as described herein. Such mixture of hydrogen and organic chloride compound can be useful to not only activate the catalyst composition, but also to pretreat such catalyst composition.

Generally, a process of the present invention is conducted in a conversion zone wherein is contained a catalyst composition of the present invention under conversion conditions that provide for contacting at least one isoparaffin and at least one $C_5$ olefin to provide for converting the at least one isoparaffin and the at least one $C_5$ olefin. Conversion conditions include any temperature suitable for conducting a process of the present invention. Generally, the conversion conditions comprise a temperature in the range of from about 30° C. to about 500° C., preferably in the range from about 40° C. to about 400° C., and more preferably in the range of from about 50° C. to about 300° C.

The conversion conditions further comprise a conversion pressure that can be any pressure sufficient to provide for a process of the present invention, comprising contacting at least one isoparaffin and at least one $C_5$ olefin, and is generally sufficient to maintain the reactants and products substantially in the liquid phase. The conversion pressures will generally be in the range of from about 40 pounds gauge pressure per square inch (psig) to about 1000 psig, preferably in the range of from about 100 psig to about 750 psig, and more preferably in the range of from about 200 psig to about 500 psig. With all reactants in the liquid phase, increased pressure has no significant effect upon the conversion(s) of the present invention.

The conversion conditions further comprise a contact time for the hydrocarbon conversion(s) of a process of the present invention in a conversion zone in the presence of a catalyst composition of the present invention that can be any time period that suitably provides for a conversion process of the present invention. Generally, the contact time is in the range from about from about 0.05 minute to about 2 hours, preferably in the range of from about 0.05 minute to about 60 minutes.

Generally, a weight ratio of catalyst composition to total hydrocarbon is any weight ratio that provides for a process of the present invention. Generally, a weight ratio of catalyst composition to total hydrocarbon is in the range of from about 0.01:1 to about 20:1, preferably in the range of from about 0.5:1 to about 15:1, and more preferably in the range of from about 1:1 to about 10:1.

A process of the present invention, comprising contacting at least one isoparaffin and at least one $C_5$ olefin, can be carried out either as a batch or continuous type of operation, although it is preferred for economic reasons to carry out the process continuously. It has been generally established that in alkylation processes, the more intimate the contact between the hydrocarbon-containing fluid, i.e., feedstock, and the catalyst, the better the quality of alkylate product obtained. With this in mind, a process of the present invention, when operated as a batch operation, is characterized by the use of vigorous mechanical stirring or shaking of the reactants and catalyst composition.

The conversion zone design is not critical, except that sufficient dispersion of the hydrocarbon into the catalyst composition should be achieved under well-mixed conditions. A preferred reactor design is a plug-flow fixed bed reactor.

An example process of the present invention comprises contacting at least one isoparaffin comprising isopentane and at least one $C_5$ olefin selected from the group consisting of 1-pentene, 2-methyl-1-butene, 2-methyl-2-butene, and combinations thereof in the presence of a catalyst composition of the present invention under conversion conditions to provide at least one product hydrocarbon comprising from about 4 to about 10 carbon atoms per molecule, preferably comprising from about 6 to about 9 carbon atoms per molecule. Preferably, the at least one isoparaffin and the at least one $C_5$ olefin are present in a hydrocarbon-containing fluid and that the process provides for a product comprising a larger amount of hydrocarbons comprising from about 6 to about 9 carbon atoms per molecule than were present before the contacting of at least one isoparaffin and at least one $C_5$ olefin. The converting can be selected from the group consisting of isomerizing, oligomerizing, disproportionating, cleaving, and the like and combinations thereof.

One example converting that may occur during a process of the present invention comprises contacting at least one isoparaffin and at least one $C_5$ olefin to provide for an intermediate hydrocarbon containing 10 or more carbon atoms per molecule followed by subsequent converting, such as, but not limited to, disproportionating or cleaving to provide for hydrocarbons having less than 10 carbon atoms per molecule, preferably having from about 6 to about 9 carbon atoms per molecule. Another example converting that may occur during a process of the present invention comprises oligomerizing where, during contacting of at least one isoparaffin and at least one $C_5$ olefin according to a process of the present invention, two or more $C_5$ olefins may be dimerized to provide a product having 10 carbon atoms per molecule. Another example converting that may occur during a process of the present invention comprises at least one $C_5$ olefin comprising 1-pentene that is isomerized, also referred to as double bond isomerization, to provide a 2-pentene. The various converting reactions as described herein may occur separately, simultaneously, and in combinations thereof during a process of the present invention.

A catalyst composition of the present invention may be added by injection directly into a conversion zone, or may be mixed with a hydrocarbon-containing fluid containing at least one isoparaffin and at least one $C_5$ olefin, or may be mixed with fresh and/or circulating catalyst composition, or with a stream of mixed hydrocarbon-containing fluid and catalyst composition, or the like and combinations thereof. Downstream from the conversion zone, the catalyst composition can be preferably separated from the product stream, mixed with fresh and/or circulating catalyst composition, and recycled to the conversion zone. The particular separation technique selected depends upon the characteristics of the catalyst composition and the desired reaction products. Selection of such separation techniques is within the skill in the art.

Another example process of the present invention comprises separating hydrocarbons containing 5 carbon atoms per molecule, such as $C_5$ olefins, from gasoline, routing the $C_5$ hydrocarbons to a conversion zone comprising a reactor containing a catalyst composition of the present invention and separating the resulting products into a $C_3/C_4$ fraction containing hydrocarbons having from about 3 to about 4 carbon atoms, a $C_5$ fraction containing hydrocarbons containing 5 carbon atoms per molecule, and a $C_6+$ fraction containing hydrocarbons containing 6 or more carbon atoms per molecule. The $C_3/C_4$ fraction can be sent to an alkylation unit, the $C_5$ fraction can be recycled to the conversion zone, and the $C_6+$ fraction can be further separated into a gasoline range fraction and a diesel range fraction. The diesel range product can be hydrogenated to provide a blend stock with little to no sulfur, olefins, or aromatics.

During a process of the present invention, impurities present in the feed stream(s) can contribute to a rapid decrease in catalyst activity. Such catalyst deactivating effect is counteracted in a process of the present invention by the presence of an additive comprising an organic chloride compound. An organic chloride compound suitable as an additive in a process of the present invention comprises any organic chloride compound that helps deactivate or counter the effects of catalyst deactivation during a process of the present invention comprising contacting at least one isoparaffin and at least one $C_5$ olefin. Examples of a suitable organic chloride compound include, but are not limited to, tetrachloroethylene (TCE) (also referred to as perchloroethylene or PCE), ethylaluminum dichloride, carbon tetrachloride, hexachloroethane, 1-chlorobutane, 2-chlorobutane, 1-chloro-2-methylpropane, 2-chloro-2-methylpropane, and the like and combinations thereof. A preferred organic chloride compound comprises tetrachloroethylene. A more preferred organic chloride compound comprises a combination of tetrachloroethylene and ethylaluminum dichloride. During a process of the present invention comprising contacting at least one isoparaffin and at least one $C_5$ olefin, the additive comprising an organic chloride compound can be injected into the hydrocarbon-containing fluid, any of the individual feed streams, or combinations thereof.

An effective amount of an organic chloride compound, i.e., the concentration of organic chloride compound, in a process of the present invention comprising contacting at least one isoparaffin and at least one $C_5$ olefin is in the range of from about 0.01 ppm organic chloride compound to about 1000 ppm organic chloride compound (i.e., about 0.01 part by weight organic chloride compound per million parts by weight of total hydrocarbon to about 1000 parts by weight organic chloride compound per million parts by weight of total hydrocarbon). Preferably, a concentration of organic chloride compound is in the range of from about 0.05 ppm organic chloride compound to about 900 ppm organic chloride compound, and more preferably in the range of from about 0.1 ppm organic chloride compound to about 800 ppm organic chloride compound. The amount of additive comprising an organic chloride compound injected into the hydrocarbon-containing fluid, any of the individual feed streams, or combinations thereof, should be such that the concentrations of the organic chloride compound recited herein can be maintained. The injection of the organic chloride compound can be conducted continuously or intermittently, i.e., pulsed.

After a catalyst composition the present invention has been deactivated by, for example, coke deposition, or feed poisons, to the extent that the fluid conversion and/or the production of hydrocarbons having from 6 to 9 carbon atoms per molecule has become unsatisfactory, the catalyst composition can be regenerated by, for example, calcining to burn off deposited coke and other carbonaceous materials, such as oligomers or polymers, preferably at a temperature in the range of from about 100° C. to about 500° C. The optimal time periods for calcining depend generally on the types and amounts of the deactivating deposits on the catalyst composition and on the calcination temperatures. These optimal time periods can be determined by those possessing ordinary skill in the art and are omitted herein for the interest of brevity. An example regeneration procedure comprises subjecting a deactivated catalyst composition of the present invention to an activating under an activating condition as described herein.

Another example regeneration procedure comprises subjecting a deactivated catalyst composition of the present invention to a hydrogen treatment comprising stopping the hydrocarbon-containing fluid feed, removing liquid hydrocarbon components from the conversion zone, and purging with an inert gas for a time period in the range of from about 0.01 hour to about 48 hours, preferably about 10 minutes. The temperature is then increased to about 300° F. to about 700° F., preferably about 350° F. to about 550° F., and a flow of hydrogen is started to the conversion zone at a flow rate sufficient to achieve a gas hourly space velocity in the range of from about 0.01 hours$^{-1}$ to about 100 hour$^{-1}$ and the hydrogen flow over the catalyst composition is maintained for a time period in the range of from about 0.01 hour to about 48 hours, preferably about 2 hours to about 24 hours. The temperature can then be controlled to the desired conversion condition temperature as described herein and the hydrocarbon-containing fluid feed can be reintroduced. In addition, after the flow of hydrogen is stopped, a flow of nitrogen can be started at a temperature of about 300° F. to about 700° F., preferably about 350° F. to about 550° F., and at a flow rate sufficient to achieve a gas hourly space velocity in the range of from about 0.01 hour$^{-1}$ to about 100 hour$^{-1}$ and the nitrogen flow over the catalyst composition can be maintained for a period of time in the range of from about 0.01 hour to about 48 hours, preferably about 2 hours to about 24 hours, before the reintroduction of the hydrocarbon-containing fluid feed. Also, the flow of hydrogen can be substituted with a mixture of hydrogen and an organic chloride compound as described herein. Substituting with such a mixture can be an option when conducting a process of the present invention utilizing the organic chloride compound addition as described herein.

The following examples are presented to further illustrate the present invention and are not to be construed as unduly limiting the scope of the present invention. In the following Examples and Tables the following abbreviations are used: C2 is ethane; C3 is propane; C3= is propylene; iC4 is isobutane; iC4= is isobutene; 1C4= is 1-butene; nC4 is normal butane; 2C4=t is trans-2-butene; NeoC5 is neopentane (i.e., 2,2-dimethylpropane); 2C4=c is cis-2-butene; 2C4=is total 2-butenes; 3MB1 is 3-methyl-1-butene; iC5 is isopentane; iC5= is isopentene; 1C5= is 1-pentene; 2MB1 is 2-methyl-1-butene; nC5 is normal pentane; C5= is total pentenes; 2C5=t is trans-2-pentene; 2C5=c is cis-2-pentene; 2C5= is total 2-pentenes; 2MB2 is 2-methyl-2-butene; ?C1–C5 is unidentified components eluting in the C1–C5 (methane-pentane) region; C6–C8 is total components having 6 to 8 carbon atoms per molecule without regard to the compound type (i.e., paraffins, olefins, aromatics, naphthenes, and the like); C9 is total components having 9 carbon atoms per molecule regardless of type; C6+ is total components with at least 6 or more carbon atoms per molecule regardless of type; C10+ is total components with at least 10 or more carbon atoms per molecule regardless of type; Conv is conversion; Lights is total hydrocarbons having 4 or less carbon atoms per molecule; TOS is Time on Stream; Rxtr is reactor; Cl is organic chloride compound; TSP is Temperature Set Point; Temp. is temperature; and MoHPA is 12-molybdophosphoric acid. C6–C8, C9, C6+, and C10+ were determined by the relative retention times on a gas chromatograph column that allowed components to elute in the order of increasing boiling point. All numbers in the tables are weight percent unless otherwise indicated.

EXAMPLE 1

Example 1 illustrates the preparation of several catalyst compositions that were subsequently tested as catalysts in a process comprising contacting an isoparaffin and a $C_5$ olefin.

Catalyst A: (MoHPA/Zeolite Beta/Pt) A solution of 3.80 grams of 12-molybdophophoric acid in about 25 mL of distilled water was prepared and approximately half of the solution was added to a 17.0 gram quantity of zeolite beta (Si/Al ratio of 150) under incipient wetness conditions. A 1.20 gram quantity of a platinum (IV) chloride ($PtCl_4$) solution (10% Platinum) was then added to the remaining half of the aqueous 12-molybdophophoric acid solution and then slowly added to the zeolite beta. After addition, the resulting material was then was dried in a vacuum oven at about 80° C. for about three hours to provide a final weight of 20.42 grams. The resulting dried material was then mixed with a 2.5 gram quantity of bentonite clay filler and about 0.85 mL of distilled water to provide a paste that was extruded through a 25 mL plastic syringe. The resulting extrudate was then dried in a drying oven at about 115° C. for about 18 hours. The resulting dried extrudate was then granulated to provide pieces of about 0.125 inches to about 0.25 inches in length. A 9.99 gram quantity of the extrudate pieces (26.5 mL) was mixed with about 10 mL of inert Alundum and charged to a tubular reactor described herein in Example 2 and heated to about 149° C. and treated with hydrogen at an initial flow rate of 5 mL/min that was increased to 25 mL/min. After about two hours, the reactor was purged with nitrogen followed by the introduction of a hydrocarbon-containing fluid feed.

Catalyst B: (MoHPA/$SiO_2$) A solution of 3.50 grams of 12-molybdophosphoric acid in about 25 mL of distilled water was prepared and added to a 5.7 gram quantity of Davison grade 57 silica under incipient wetness conditions. The resulting material was dried in a vacuum oven at about 85° C. for about 17 hours to provide a final weight of 8.67 grams (9.2 grams theoretical). A portion of the resulting dried material (4.0 grams) was mixed with 2.0 grams of bentonite clay filler and enough distilled water was added to make a paste sufficient to extrude through a 25 mL plastic syringe. The extrudate was then dried in a drying oven at about 115° C. for about two hours. The resulting dried extrudate was then granulated to provide pieces of about 0.125 inches to about 0.25 inches in length. A 5.34 gram quantity of the extrudate pieces was mixed with about 10 mL of inert Alundum and charged to a tubular reactor described herein in Example 2 and heated to about 121° C. and treated with hydrogen at an initial flow rate of 5 mL/min that was increased to 25 mL/min. After about three hours, the reactor was purged with nitrogen followed by the introduction of a hydrocarbon-containing fluid feed.

Catalyst C: (MoHPA/$ZnCl_2$ (10%) on alumina) In separate beakers, solutions of 2.45 grams of 12-molybdophosphoric acid in about 25 mL of distilled water and 2.24 grams of zinc chloride in about 25 mL of distilled water were prepared and added (in three portions) to an 11.37 gram quantity of alumina (Condea Pural SB-1) under incipient wetness conditions. The resulting material was dried in a vacuum oven at about 80° C. between additions. After the final loading, the resulting material was dried in a vacuum oven at about 60° C. for about 18 hours to provide a final weight of 14.79 grams. The resulting dried material was then moistened with enough distilled water to provide a paste that was extruded through a 25 mL plastic syringe. The resulting extrudate was then dried in a vacuum oven at about 60° C. for about 18 hours. The resulting dried extrudate was then granulated to provide pieces of about 0.125 inches to about 0.25 inches in length. A 14.15 gram quantity of dried extrudate was obtained. A 6.07 gram quantity of the extrudate pieces (10 mL) was mixed with about 10 mL of inert Alundum and charged to a tubular reactor described herein in Example 2 and heated to about 139° C. and treated with hydrogen at an initial flow rate of 5 mL/min that was increased to 25 mL/min. After about four hours, the reactor was purged with nitrogen followed by the introduction of a hydrocarbon-containing fluid feed.

Catalyst D: (MoHPA/$ZnCl_2$ (2%) on alumina) In separate beakers, solutions of 2.77 grams of 12-molybdophosphoric acid in about 10 mL of distilled water and 0.37 grams of zinc chloride in about 10 mL of distilled water were prepared and added in three portions to a 13.37 gram quantity of alumina (Condea Pural SB-1) under incipient wetness conditions. The resulting material was dried in a vacuum oven at about 80° C. between additions. After the final loading, the resulting material was dried in a vacuum oven at about 60° C. for about 18 hours and reweighed. After weighing, enough water was added to provide a paste that was extruded through a 25 mL plastic syringe. The resulting extrudate was then dried in a vacuum oven at about 60° C. for about 18 hours. The resulting dried extrudate was then granulated to provide pieces of about 0.125 inches to about 0.25 inches in length. A 14.03 gram quantity of dried extrudate was obtained. A 10.25 gram quantity of the extrudate pieces (20 mL) was mixed with about 10 mL of inert Alundum and charged to a tubular reactor described herein in Example 2 and heated to about 260° C. and treated with hydrogen at an initial flow rate of 5 mL/min that was increased to 25 mL/min. After about three hours, the reactor was purged with nitrogen.

EXAMPLE 2

This example illustrates the use of the catalyst compositions described herein in Example 1 as catalyst compositions in a process comprising contacting an isoparaffin and a $C_5$ olefin.

The reactor system consisted of a syringe pump for delivering a hydrocarbon-containing fluid feed, a tubular reactor (0.75 inch diameter and 18 inches length, with a thermowell in the center), back-pressure regulators, sampling components, and product collection equipment. The hydrocarbon-containing fluid feed was drawn into the syringe pump, then pumped downflow across the catalyst bed (centered in the reactor with inert Alundum below and above the active catalyst bed; each separated by glass wool). The reactor was contained inside an electrically heated furnace, the temperature of which was set and monitored independently from the reactor bed temperature disclosed in the Tables.

After a Time On Stream (TOS) as indicated in Table 1, each catalyst composition was subjected to a regeneration comprising a hydrogen treatment according to the following process. The hydrocarbon-containing fluid feed was stopped and the reactor was drained of liquid components. After purging the reactor for about 10 minutes with nitrogen, the temperature set point was increased from 300° F. to 350° F.

Hydrogen flow was started at a rate of 25 standard cubic centimeters per minute (sccm) and increased to 50 sccm over the course of two hours and then stopped. The flow of nitrogen was then started at 50 sccm and allowed to flow for about 18 hours Table 1 discloses a comparison of the results obtained utilizing catalyst compositions A, B and C described herein in Example 1. The results disclose that catalyst composition C comprising 12-molybdophosphoric acid, zinc, and a support component comprising alumina provided for an increase in C6–C8 and C9 components compared to catalyst compositions A and B. Such components are valuable as gasoline components and have lower vapor pressure than the parent C5 olefins. Catalyst composition C also provided for a decrease in C10+ components compared to catalyst compositions A and B. Such components can negatively influence gasoline distillation index (DI) values by increasing the T50 and T90 values. Catalyst composition C also provided for an increase in total 2-butenes compared to catalyst compositions A and B. The 2-butenes are valuable components for alkylation feeds, and high octane, low vapor pressure alkylate can be prepared from such 2-butenes. In addition, catalyst composition C provided for an 87.5% restoration of activity after the catalyst regeneration (hydrogen treatment). The restoration of activity was based on the extent of conversion obtained after the catalyst regeneration as a percentage of the extent of conversion obtained with a fresh catalyst composition. No response was noted for catalyst composition B when subjected to the same hydrogen treatment.

TABLE 1

| Catalyst | A (MoHPA/ Zeo B/Pt) | B (MoHPA/ SiO2) | C (MoHPA/ Al2O3/ZnCl2) |
|---|---|---|---|
| % MoHPA | 18.2 | 40 | 15.3 |
| % Pt | 0.6 | 0 | 0 |
| % ZnCl2 | 0 | 0 | 13.9 |
| TOS, Hrs | 7.5 | 4 | 4 |
| Rxtr Temp., ° F. | 272 | 251.4 | 315 |
| Feed (wt %) | | | |
| Lights | 0.15 | 0 | 0.308 |
| iC5 | 49.49 | 49.33 | 49.77 |
| 1C5 = | 25.31 | 25.35 | 25.12 |
| iC5 = | 24.05 | 25.32 | 23.50 |
| nC5 | 0.25 | 0.00 | 0.25 |
| 2C5 = | 0.00 | 0.00 | 0.04 |
| C6+ | 0.75 | 0.00 | 1.00 |
| Product (wt %) | | | |
| C3 | 0.000 | 0.000 | 0.000 |
| iC4 | 0.040 | 0.030 | 0.063 |
| nC4 | 0.000 | 0.000 | 0.050 |
| C3 = | 0.000 | 0.000 | 0.002 |
| 1C4 =/iC4 = | 0.030 | 0.110 | 0.317 |
| 2C4 = | 0.000 | 0.000 | 0.127 |
| iC5 | 50.83 | 50.82 | 53.06 |
| nC5 | 0.29 | 0.03 | 0.27 |
| C5 = | 24.48 | 33.298 | 36.81 |
| C6–C8 | 0.91 | 1.13 | 1.95 |
| C9 | 0.43 | 0.96 | 2.97 |
| C10+ | 22.02 | 13.59 | 4.08 |
| 1C5 = Conversion | 75.28 | 57.95 | 36.88 |
| iC5 = Conversion | 71.73 | 58.98 | 44.65 |
| % Activity Restored After Hydrogen Treatment | 100 | No Response | 87.5 |

MoHPA = 12-Molybdophosphoric acid
Zeo B = Zeolite Beta
1C4 =/iC4 = is total of both components

EXAMPLE 3

Figure 2:
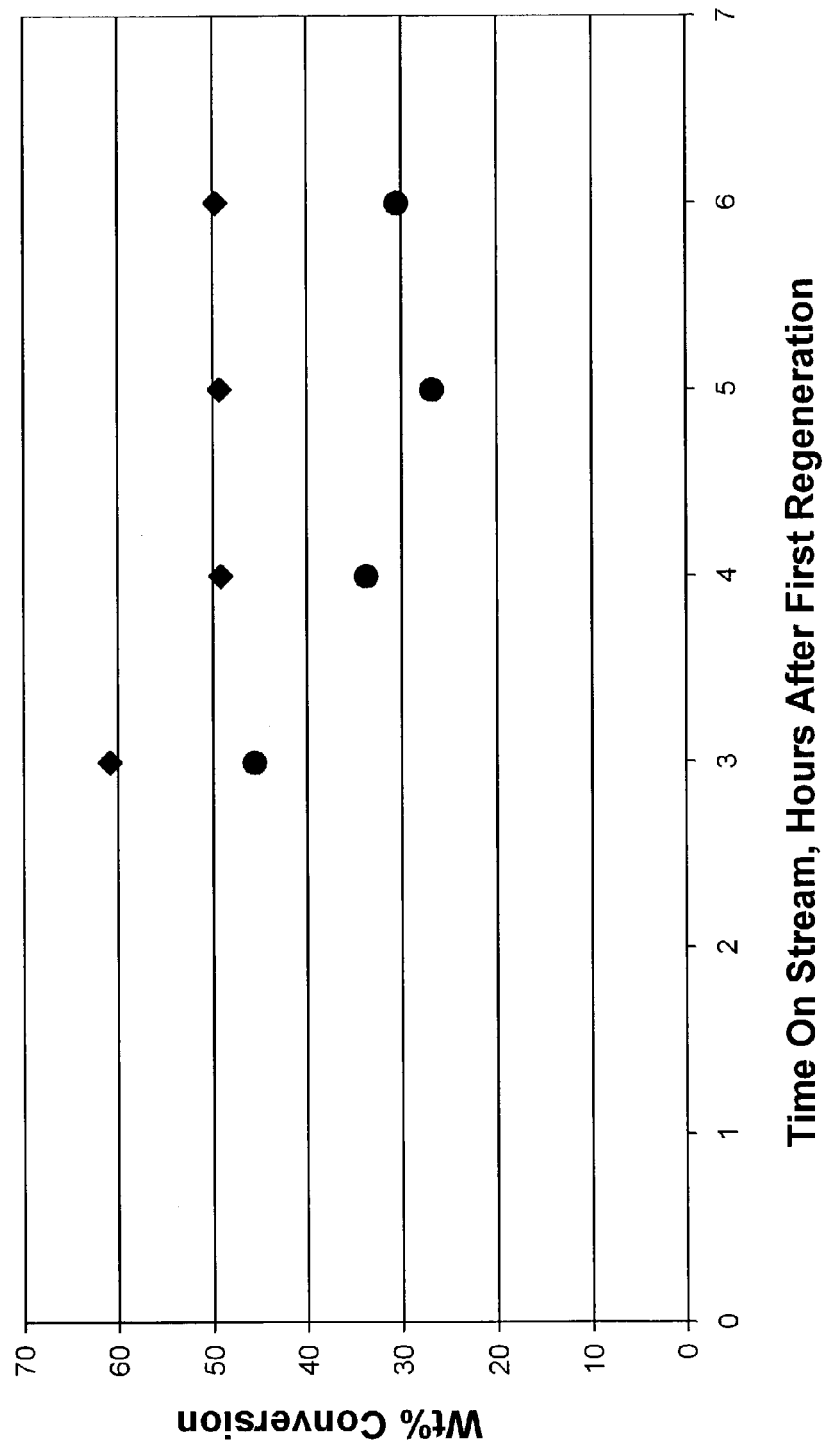
FIG. 2 is a graph of the C5=conversions after the first regeneration of catalyst composition C described herein in Example 1 utilizing the conditions described herein in Example 3 and based on the data disclosed in Table 4.
Figure 3:
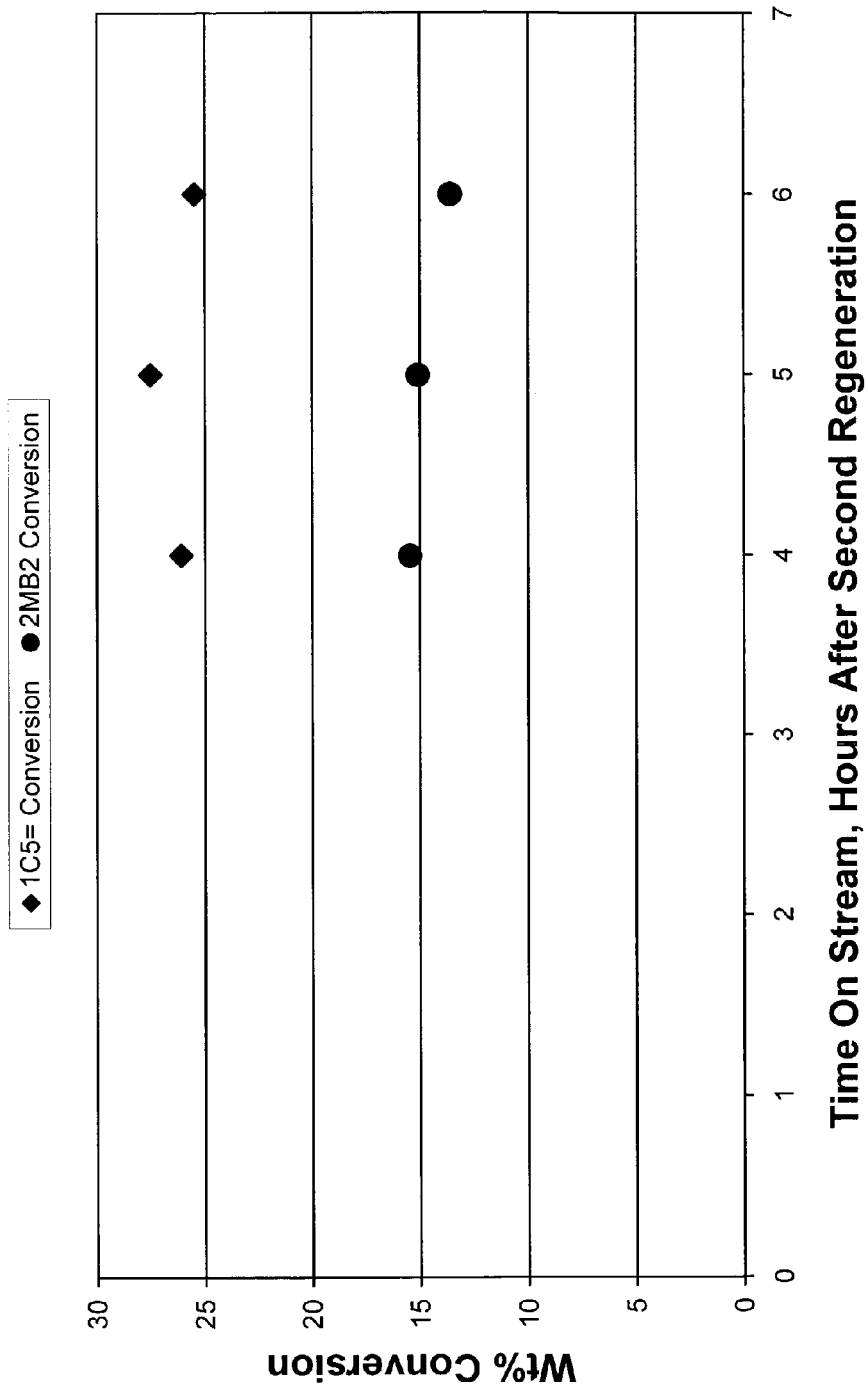
FIG. 3 is a graph of the C5=conversions after the second regeneration of catalyst composition C described herein in Example 1 utilizing the conditions described herein in Example 3 and based on the data disclosed in Table 5.

Example 3 illustrates a process of the present invention utilizing catalyst composition C (MoHPA/ZnCl$_2$ (10%) on alumina) described herein in Example 1. The reactor system described herein in Example 2 was utilized. The process was initially conducted over a time period of about six hours. The hydrocarbon-containing fluid feed utilized in Example 3 comprised the C5 fraction from fluidized catalytically cracked (FCC) gasoline utilizing model compounds. The composition of the hydrocarbon-containing fluid feed utilized in Example 3 is disclosed herein in Table 2. Table 3 discloses the 1-pentene (1C5=) conversion, 2-methyl-2-butene (2MB2) conversion, and the reactor temperature after three, four and six hour time periods on stream. The results disclosed in Table 3 are disclosed graphically herein in FIG. 1. After six hours, catalyst composition C was subjected to a first regeneration according to the following process. The hydrocarbon-containing fluid feed was stopped and the reactor was drained of liquid components. After purging the reactor for about 10 minutes with nitrogen, the temperature set point was increased from 300° F. to 350° F. Hydrogen flow was started at a rate of 25 standard cubic centimeters per minute (sccm) and increased to 50 sccm over the course of two hours and then stopped. The flow of nitrogen was then started at 50 sccm and continued for about 18 hours. After the first regeneration, the process was continued for approximately six hours. Table 4 discloses the 1-pentene (1C5=) conversion, 2-methyl-2-butene (2MB2) conversion, and the reactor temperature after three, four, five, and six hour time periods on stream after the first regeneration. The results disclosed in Table 4 are disclosed graphically herein in FIG. 2. After the six hour run after the first regeneration, catalyst composition C was subjected to a second regeneration similar to the first regeneration except the temperature set point was increased to 500° F. to provide a catalyst composition temperature of about 530° F. Catalyst composition C was subjected to a second regeneration according to the following process. The hydrocarbon-containing fluid feed was stopped and the reactor was drained of liquid components. After purging the reactor for about 10 minutes with nitrogen, the temperature set point was increased from 300° F. to 500° F. to provide a catalyst composition temperature of about 530° F. Hydrogen flow was started at a rate of 25 standard cubic centimeters per minute (sccm) and increased to 50 sccm over the course of two hours and then stopped. The flow of nitrogen was then started at 50 sccm and continued for about 18 hours. After the second regeneration, the process was continued for approximately six hours. Table 5 discloses the 1-pentene (1C5=) conversion, 2-methyl-2-butene (2MB2) conversion, and the reactor temperature after four, five, and six hour time periods on stream after the second regeneration. The results disclosed in Table 5 are disclosed graphically herein in FIG. 3.

The data disclosed herein in Tables 3, 4, and 5 clearly demonstrate that catalyst composition C demonstrated good regenerability after the first regeneration, but the second regeneration had less of an impact on restoring catalyst composition activity.

TABLE 2

| | Feed |
|---|---|
| C3 = | 0.000 |
| iC4 | 0.146 |
| iC4 = | 0.000 |

TABLE 2-continued

| | Feed |
|---|---|
| nC4 | 0.049 |
| 2C4 = t | 0.000 |
| NeoC5 | 0.113 |
| 2C4 = c | 0.000 |
| 3MB1 | 0.000 |
| iC5 | 49.772 |
| 1C5 = | 25.118 |
| 2MB1 | 1.489 |
| nC5 | 0.251 |
| 2C5 = t | 0.028 |
| 2C5 = c | 0.015 |
| 2MB2 | 22.010 |
| ?C1–C5 | 0.006 |
| C6–C8 | 0.840 |
| C9 | 0.073 |
| C10+ | 0.087 |
| Total | 99.996 |

TABLE 3

| | TOS, hours | | |
|---|---|---|---|
| | 3 | 4 | 6 |
| 1C5 = Conversion | 69.45 | 36.88 | 30.49 |
| 2MB2 Conversion | 73.23 | 44.65 | 36.61 |
| Reactor Temp., °F. | 315.2 | 314 | 312.2 |

TABLE 4

| | Time On Stream, hours after first regeneration | | | |
|---|---|---|---|---|
| | 3 | 4 | 5 | 6 |
| 1C5 = Conversion | 60.8 | 49.1 | 49.2 | 49.61 |
| 2MB2 Conversion | 45.51 | 33.64 | 26.73 | 30.39 |
| Reactor Temp., °F. | 367.2 | 369.1 | 368.1 | 366.5 |

TABLE 5

| | Time On Stream, hours after second regeneration | | |
|---|---|---|---|
| | 4 | 5 | 6 |
| 1C5 = Conversion | 26.09 | 27.52 | 25.48 |
| 2MB2 Conversion | 15.45 | 15.08 | 13.59 |
| Reactor Temp., °F. | 366.9 | 366.7 | 368.2 |

EXAMPLE 4

Example 4 illustrates a process of the present invention comprising the addition of an organic chloride compound.

Catalyst composition D (MoHPA/ZnCl$_2$ (2%) on alumina) described herein in Example 1 and the reactor system described herein in Example 2 were utilized. Catalyst composition D was pre-treated by heating to 500° F. under a flow of hydrogen at a flow rate of 25 standard cubic centimeters per minute (sccm) and a flow of an organic chloride compound comprising a mixture of tetrachloroethylene (TCE) and ethylaluminum dichloride (EADC) at a flow rate of 20 microliters per hour for about 2 hours. The TCE/EADC mixture, comprising 100 mL tetrachloroethylene (TCE) and 80 microliters of pure ethylaluminum dichloride (EADC) prepared beforehand in an inert atmosphere enclosure, was charged to a syringe-type pump under a nitrogen atmosphere and the flow rate of the pump was adjusted to deliver the 20 microliters per hour flow to the reactor. The hydrogen and organic chloride compound flows were then stopped. The temperature set point was reduced to 350° F. and the hydrocarbon-containing fluid feed was then introduced when the top of the catalyst bed was 335° F. The process was initially conducted over a time period of about four hours. The composition of the hydrocarbon-containing fluid feed is disclosed herein in Table 6. Table 6 discloses the composition of the initial hydrocarbon-containing fluid feed as well as the composition of the hydrocarbon-containing fluid feed that was adjusted after about 10 hours total time on stream during a process of the present invention.

Table 7 discloses the results obtained after two, three, and four hour time periods on stream. Table 7 discloses the 1-pentene (1C5=) conversion, 2-methyl-2-butene (2MB2) conversion, the reactor temperature, and temperature set point (TSP). No organic chloride compound was added during the first four hours on stream. The results disclosed in Table 7 are disclosed graphically herein in FIG. 4. After about four hours, catalyst composition D was subjected to a first regeneration according to the following process. The hydrocarbon-containing fluid feed was stopped and the reactor was drained of liquid components. After purging the reactor for 10 minutes with nitrogen, the temperature set point was increased from 350° F. to 500° F. Hydrogen flow was then started at a rate of 25 sccm along with an organic chloride compound comprising a mixture of tetrachloroethylene (TCE) and ethylaluminum dichloride (EADC) added at a rate of 20 microliters per hour. The TCE/EADC mixture, prepared beforehand as described herein, was charged to a syringe-type pump under a nitrogen atmosphere and the flow rate of the pump was adjusted to deliver the 20 microliters per hour flow to the reactor. After about 2.5 hours, the hydrogen and organic chloride compound flows were stopped. Nitrogen flow was then started at 50 sccm and the nitrogen flow was maintained for about 18 hours with the temperature set point reduced to 350° F.

Figure 5:
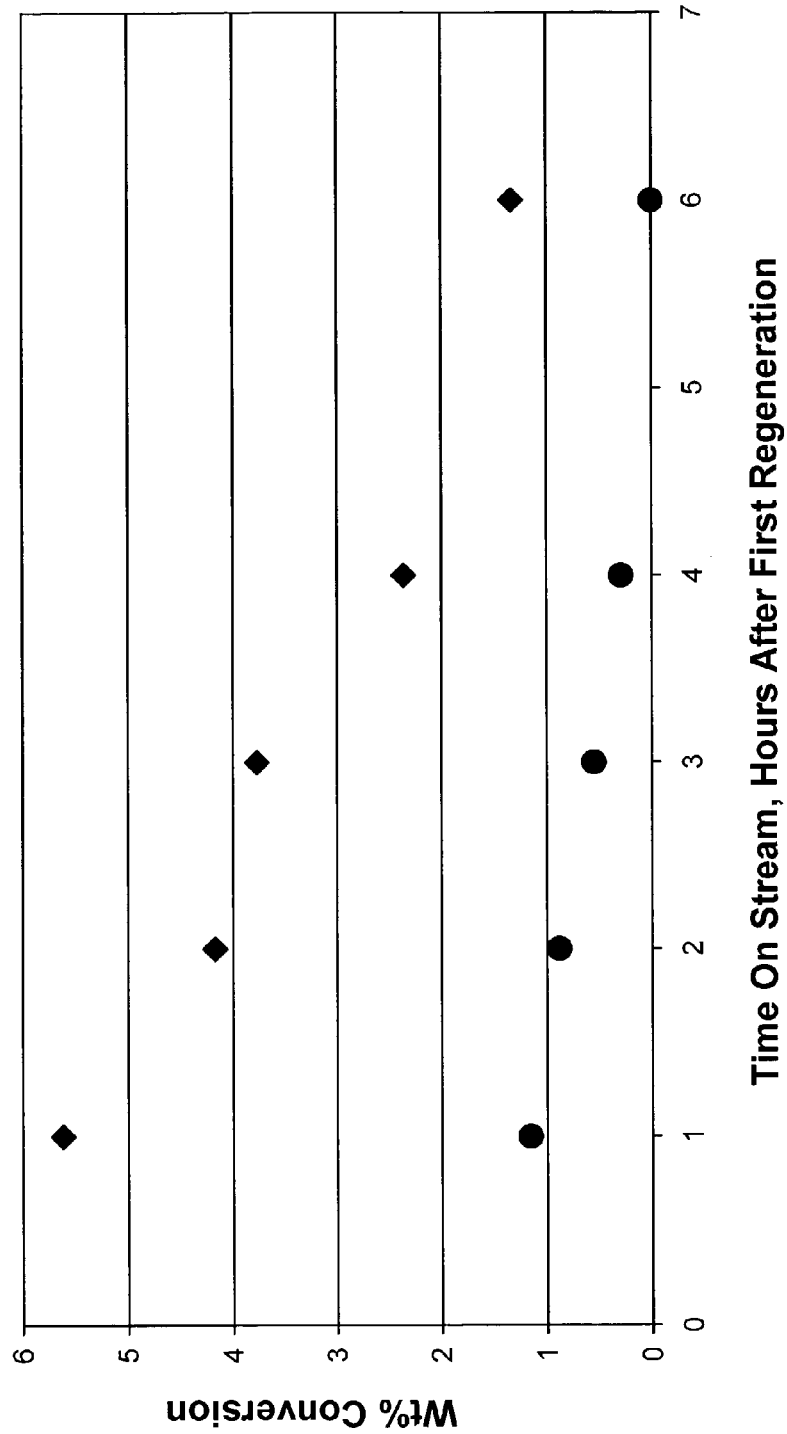
FIG. 5 is a graph of the C5=conversions with a 20 microliter per hour organic chloride compound addition utilizing catalyst composition D described herein in Example 1 utilizing the conditions described herein in Example 4 and based on the data disclosed in Table 8.

After the first regeneration, the process was continued for about six hours. During the six hours on stream after the first regeneration (hydrogen treatment), an organic chloride compound comprising a mixture of tetrachloroethylene (TCE) and ethylaluminum dichloride (EADC) was added at a rate of 20 microliters per hour. The TCE/EADC mixture, comprising 100 mL tetrachloroethylene (TCE) and 80 microliters of pure ethylaluminum dichloride (EADC) prepared beforehand in an inert atmosphere enclosure, was charged to a syringe-type pump under a nitrogen atmosphere and the flow rate of the pump was adjusted to deliver the 20 microliters per hour flow to the reactor. Table 8 discloses the 1-pentene (1C5=) conversion, 2-methyl-2-butene (2MB2) conversion, reactor temperature, organic chloride compound (Cl) feed rate, and temperature set point at one hour intervals over the six hour time period on stream after the first regeneration. The results disclosed in Table 8 are disclosed graphically herein in FIG. 5. After about six hours time on stream after the first regeneration, the hydrocarbon-containing fluid feed was adjusted to utilize a hydrocarbon-containing fluid feed composition as described herein in Table 6 under Feed #2.

After about six hours time on stream after the first regeneration (after about 10 hours total time on stream) catalyst composition D was subjected to a second regeneration similar to the first regeneration except the temperature set point was held at 400° F. and no organic chloride compound was added. Catalyst composition D was subjected to the second regeneration according to the following process. The hydrocarbon-containing fluid feed was stopped and the reactor was drained of liquid components. After purging the reactor for 10 minutes with nitrogen, the temperature set point was increased from 350° F. to 400° F. Hydrogen flow was then started at a rate of 25 sccm. After about 2.5 hours, the hydrogen flow was stopped. Nitrogen flow was then started at 50 sccm and the nitrogen flow was maintained for about 18 hours with the temperature set point reduced to 350° F.

Figure 6:
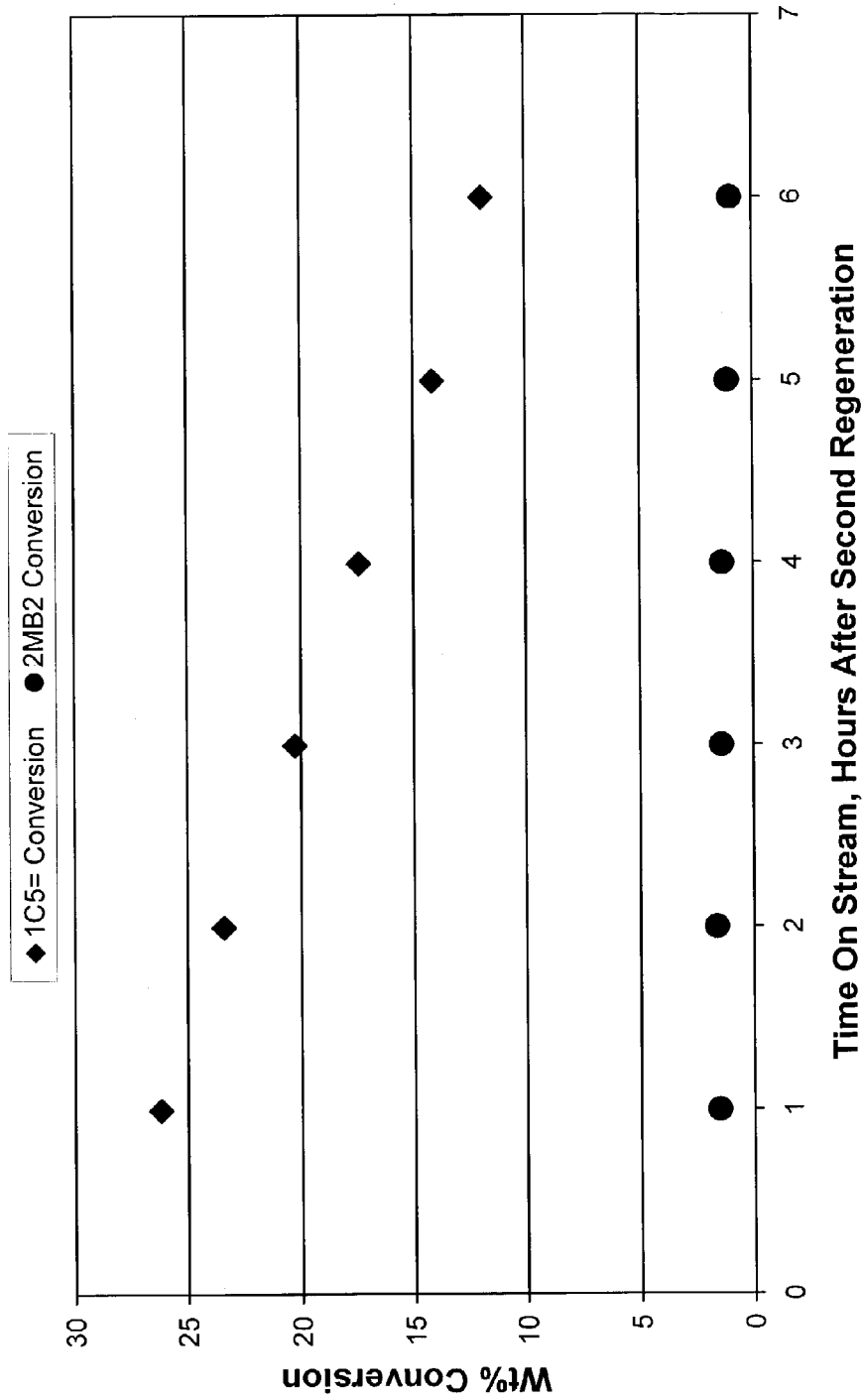
FIG. 6 is a graph of the C5=conversions with 40 microliter per hour organic chloride compound addition utilizing catalyst composition D described herein in Example 1 utilizing the conditions described herein in Example 4 and based on the data disclosed in Table 9.

After the second regeneration, the rate of organic chloride compound addition comprising the mixture of tetrachloroethylene (TCE) and ethylaluminum dichloride (EADC) was increased to 40 microliters per hour and the process was continued for about six hours. Table 9 discloses the 1-pentene (1C5=) conversion, 2-methyl-2-butene (2MB2) conversion, reactor temperature, organic chloride compound (Cl) feed rate, and temperature set point at one-hour intervals over the additional six hour time period on stream after the second regeneration. The results disclosed in Table 9 are disclosed graphically herein in FIG. 6.

TABLE 6

|  | Feed #1 | Feed #2 |
|---|---|---|
| C2 | 0.000 | 0.000 |
| C3 | 0.000 | 0.000 |
| iC4 | 0.038 | 0.040 |
| iC4 = | 0.000 | 0.000 |
| nC4 | 0.052 | 0.048 |
| 2C4 = t | 0.000 | 0.000 |
| NeoC5 | 0.125 | 0.118 |
| 2C4 = c | 0.000 | 0.000 |
| 3MB1 | 0.000 | 0.000 |
| iC5 | 52.564 | 50.305 |
| 1C5 = | 23.912 | 24.988 |
| 2MB1 | 1.457 | 1.571 |
| nC5 | 0.267 | 0.290 |
| 2C5 = t | 0.000 | 0.014 |
| 2C5 = c | 0.000 | 0.012 |
| 2MB2 | 20.964 | 21.924 |
| ?C1–C5 | 0.000 | 0.000 |
| C6–C8 | 0.620 | 0.690 |
| C9 | 0.000 | 0.000 |
| C10+ | 0.000 | 0.000 |
| Total | 100.000 | 100.000 |

TABLE 7

(No Organic Chloride Compound Addition)

|  | TOS, hours | | |
|---|---|---|---|
|  | 2 | 3 | 4 |
| 1C5 = Conversion | 16.54 | 15.26 | 11.47 |
| 2MB2 Conversion | 2.15 | 2.86 | 2.16 |
| Reactor, ° F. | 366.3 | 363.9 | 362.2 |
| Cl Feed Rate | 0 | 0 | 0 |
| Temp. Set Point, ° F. | 350 | 350 | 350 |

TABLE 8

(20 microliter/hour Organic Chloride Compound Addition)

|  | Time On Stream, hours after first regeneration and beginning of 20 microliter/hr chloride addition | | | | | |
|---|---|---|---|---|---|---|
|  | 1 | 2 | 3 | 4 | 5 | 6 |
| 1C5 = Conversion | 5.62 | 4.17 | 3.77 | 2.36 | — | 1.33 |
| 2MB2 Conversion | 1.15 | 0.88 | 0.55 | 0.29 | — | 0 |
| Reactor, ° F. | 368.5 | 366.7 | 367.6 | 363.2 | 364.7 | 414.4 |
| Cl Feed Rate | 20 | 20 | 20 | 20 | 20 | 20 |
| Temp. Set Point, ° F. | 350 | 350 | 350 | 350 | 350 | 400 |

TABLE 9

(40 microliter/hour Organic Chloride Compound Addition)

|  | Time On Stream, hours after second regeneration and beginning of 40 microliter/hr chloride addition | | | | | |
|---|---|---|---|---|---|---|
|  | 1 | 2 | 3 | 4 | 5 | 6 |
| 1C5 = Conversion | 26.18 | 23.41 | 20.25 | 17.41 | 14.13 | 11.91 |
| 2MB2 Conversion | 1.52 | 1.62 | 1.4 | 1.35 | 1.11 | 0.96 |
| Reactor, ° F. | 512.3 | 509 | 509.7 | 506.4 | 506.8 | 506.6 |
| Cl Feed Rate | 40 | 40 | 40 | 40 | 40 | 40 |
| Temp. Set Point, ° F. | 475 | 475 | 475 | 475 | 475 | 475 |

Figure 4:
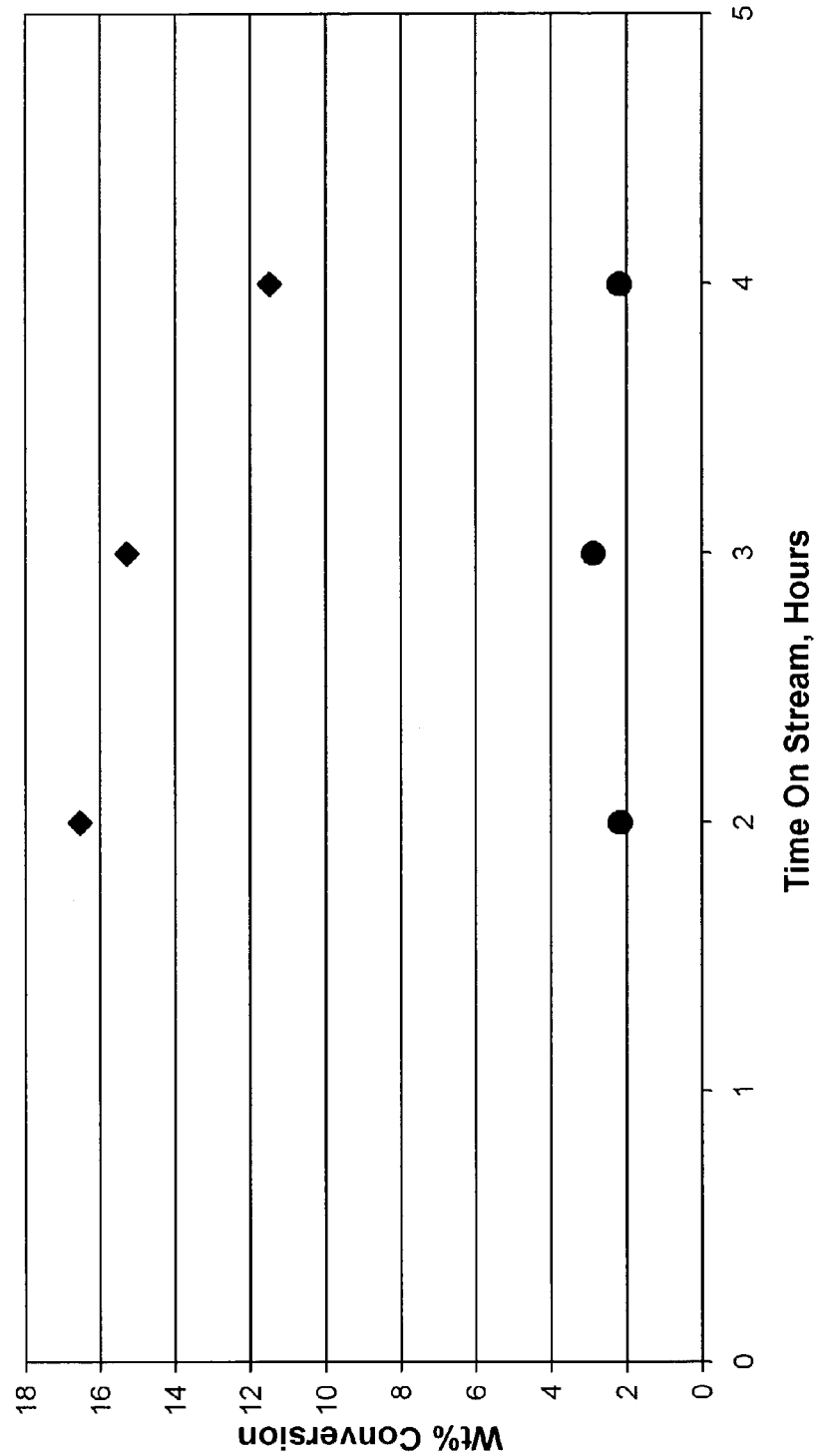
FIG. 4 is a graph of the C5=conversions with no organic chloride compound addition utilizing catalyst composition D described herein in Example 1 utilizing the conditions described herein in Example 4 and based on the data disclosed in Table 7.

The results disclosed herein in Example 4 clearly demonstrate that the rate of catalyst deactivation can be diminished utilizing a process of the present invention comprising the addition of an organic chloride compound. Comparing the results disclosed in Tables 7 and 9 (disclosed graphically in FIGS. 4 and 6, respectively), the rate of decline in catalyst composition activity is very similar even though the reactor temperatures for the data in Table 9 (FIG. 6) are approximately 140° F. higher than the reactor temperatures for the data in Table 7 (FIG. 4). In addition, comparing the results disclosed in Tables 8 and 9 (disclosed graphically in FIGS. 5 and 6, respectively) show that keeping the reactor temperature less than or equal to about 425° F. improves the restorative effects of the regenerations similar to the results disclosed herein in Example 3 (results disclosed in Tables 3, 4, and 5 and respective associated FIGS. 1, 2, and 3).

The results shown in the above examples clearly demonstrate that the present invention is well adapted to carry out the objects and obtain the ends and advantages mentioned as well as those inherent therein.

Reasonable variations, modifications, and adaptations can be made within the scope of the disclosure and the appended claims without departing from the scope of the present invention.

What is claimed is:

1. A process of preparing a catalyst composition comprising contacting a support component with a heteropoly acid and a zinc component and further wherein said contacting is selected from the group consisting of impregnating, mixing, and combinations thereof; wherein said process of preparing said catalyst composition further comprises activating under an activating condition comprising:

a temperature in the range of from about 50° C. to about 500° C.;

a pressure in the range of from about 0 pounds per square absolute to about 750 pounds per square inch absolute; and a time period in the range of from about 0.1 hour to about 30 hours; and wherein said activating condition further comprises an atmosphere comprising: 1) a reducing agent selected from the group consisting of hydrogen, hydrogen diluted with nitrogen, ammonia, hydrazine, other reducing gases, and combinations thereof, and 2) an organic chloride compound selected from the group consisting of tetrachloroethylene, ethylaluminum dichloride, carbon tetrachloride, hexachloroethane, 1-chlorobutane, 2-chlorobutane, 1-chloro-2-methylpropane, 2-chloro-2-methylpropane, and combinations thereof.

2. A process according to claim 1 wherein said impregnating is selected from the group consisting of incipient wetness impregnation, spray impregnation, and combinations thereof.

3. A process according to claim 1 wherein said process of preparing said catalyst composition further comprises, after said impregnating, subjecting to a means for forming to provide for a formed mixture comprising heteropoly acid, zinc, and support component.

4. A process according to claim 3 wherein said means for forming is selected from the group consisting of means for extruding, means for granulating, means for agglomerating, and combinations thereof.

5. A process according to claim 3 wherein said means for forming comprises a means for extruding to provide an extrudate comprising heteropoly acid, zinc, and support component.

6. A process according to claim 3 wherein said means for forming comprises a means for granulating to provide a granulate comprising heteropoly acid, zinc, and support component.

7. A process according to, claim 3 wherein said means for forming comprises a means for agglomerating to provide an agglomerate comprising heteropoly acid, zinc, and support component.

8. A process according to claim 1 wherein said process of preparing said catalyst composition further comprises drying under a drying condition comprising:

a temperature in the range of from about 20° C. to about 90° C.;

a pressure in the range of from about 0 pounds per square inch absolute to about 200 pounds per square inch absolute; and a time period in the range of from about 0.5 hours to about 40 hours.

9. A process according to claim 8 wherein said drying condition further comprises an atmosphere comprising air.

10. A process according to claim 1 wherein said process of preparing said catalyst composition further comprises calcining under a calcining condition comprising:

a temperature in the range of from about 100° C. to about 500° C.;

a pressure in the range of from 0 pounds per square inch absolute to about 750 pounds per square inch absolute; and a time period in the range of from about 0.5 hours to about 30 hours.

11. A process according to claim 10 wherein said calcining condition further comprises an atmosphere selected from the group consisting of an oxygen-containing atmosphere, nitrogen, helium, argon, and combinations thereof.

12. A process according to claim 1 wherein said organic chloride compound comprises tetrachloroethylene.

13. A process according to claim 1 wherein said heteropoly acid is selected from the group consisting 12-molybdophosphoric acid, 12-tungstophosphoric acid, molybdosilicic acid, 12-tungstosilicic acid, and combinations thereof.

14. A process according to claim 13 wherein said heteropoly acid is 12-molybdophosphoric acid.

15. A process according to claim 1 wherein said zinc component is selected from the group consisting of zinc bromide, zinc chloride, zinc iodide, zinc nitrate hydrate, zinc nitrate hexahydrate, zinc nitrate, zinc oxide, zinc perchlorate hexahydrate, zinc sulfate heptahydrate, and combinations thereof.

16. A process according to claim 15 wherein said zinc component is zinc chloride.

17. A process according to claim 1 wherein said support component is selected from the group consisting of alumina, silica, aluminasilicates, activated carbon, zeolites, oxides of the metals of Groups II, III, IV, V, and VI A of the Periodic Table of the Elements, and combinations thereof.

18. A process according to claim 1 wherein said support component is alumina.

19. A process according to claim 1 wherein a weight percent of polyatom based on the total weight of said catalyst composition is in the range of from about 0.1 to about 10.

20. A process according to claim 19 wherein said polyatom comprises molybdenum.

21. A process according to claim 1 wherein a weight percent of zinc based on the total weight of said catalyst composition is in the range of from about 0.1 to about 10.

22. A process according to claim 1 wherein a weight percent of said support component based on the total weight of said catalyst composition is in the range of from about 50 to about 99.9.

23. A composition prepared by the process of claim 1.

24. A composition prepared by the process of claim 3.

25. A composition prepared by the process of claim 8.

26. A composition prepared by the process of claim 10.

27. A composition prepared by the process of claim 13.

28. A composition prepared by the process of claim 15.

29. A composition prepared by the process of claim 17.

30. A composition prepared by the process of claim 19.

31. A composition prepared by the process of claim 20.

* * * * *